United States Patent
MacMichael et al.

(10) Patent No.: US 6,405,727 B1
(45) Date of Patent: Jun. 18, 2002

(54) INHALER MECHANISM

(75) Inventors: Donald Bruce Atherton MacMichael, Hitchin; David John Hearne, Harlington, both of (GB)

(73) Assignee: PA Knowledge Limited, Georgetown (KY)

( * ) Notice: Subject to any disclaimer, the term of this patent is extended or adjusted under 35 U.S.C. 154(b) by 0 days.

(21) Appl. No.: 09/424,442

(22) PCT Filed: May 22, 1998

(86) PCT No.: PCT/GB98/01501

§ 371 (c)(1),
(2), (4) Date: Feb. 15, 2000

(87) PCT Pub. No.: WO98/52634

PCT Pub. Date: Nov. 26, 1998

(30) Foreign Application Priority Data

May 23, 1997 (GB) ............................................. 9710634
Sep. 30, 1997 (GB) ............................................. 9720594
Jan. 15, 1998 (GB) ............................................. 9800862

(51) Int. Cl.[7] ............................................. A61M 15/00
(52) U.S. Cl. ............................. 128/203.12; 128/200.23
(58) Field of Search ................... 128/200.12, 200.14, 128/200.25, 200.21, 203.12, 203.14, 203.15, 203.21, 200.22, 200.23

(56) References Cited

U.S. PATENT DOCUMENTS

| | | | | |
|---|---|---|---|---|
| 3,789,843 A | * | 2/1974 | Armstrong et al. ......... | 128/173 |
| 3,826,413 A | * | 7/1974 | Warren ................... | 128/203.23 |
| 4,664,107 A | * | 5/1987 | Wass ..................... | 128/200.23 |
| 5,027,808 A | * | 7/1991 | Rich et al. .............. | 128/203.23 |
| 5,060,643 A | * | 10/1991 | Rich et al. .............. | 128/200.23 |
| 5,069,204 A | * | 12/1991 | Smith et al. ............. | 128/200.23 |
| 5,119,806 A | * | 6/1992 | Palson et al. ............ | 128/200.14 |
| 5,217,004 A | * | 6/1993 | Blasnik et al. .......... | 128/200.23 |
| 5,349,945 A | * | 9/1994 | Wass et al. ............. | 128/200.23 |
| 5,408,994 A | * | 4/1995 | Wass et al. ............. | 128/203.15 |
| 5,546,932 A | * | 8/1996 | Galli .................... | 128/203.15 |
| 5,826,571 A | * | 10/1998 | Casper et al. .......... | 128/200.23 |
| 6,142,339 A | * | 11/2000 | Blacker et al. ........ | 128/200.23 |

* cited by examiner

*Primary Examiner*—John G. Weiss
*Assistant Examiner*—Teena Mitchell
(74) *Attorney, Agent, or Firm*—Lee, Mann, Smith, McWilliams, Sweeney & Ohlson (57) ABSTRACT

A dosing device comprising a dispensing means for dispensing a dose material, and a dose actuation mechanism, in which the dose actuation mechanism comprises a readily deflectable member, and a cascade of at least two pivoted elements, movement of one causing movement of the other, wherein the deflectable member is moveable by the user, and its movement is transferred to the first of the cascade of pivoted elements, so as to actuate the dispensing means. A first biasing means communicates with one pivoted element so that as movement is transferred between the pivoted elements, energy stored in the first biasing means is released to increase the force associated with the movement. A dose actuating mechanism for use in a dosing inhaler is also provided.

13 Claims, 13 Drawing Sheets

INHALER MECHANISM

FIELD OF THE INVENTION

This invention concerns a dosing device and in particular relates to dosing devices for drug delivery such as injectors and inhalers, and a mechanism for use in such devices.

BACKGROUND OF THE INVENTION

In treatment for asthma and other respiratory problems, a patient may take medication into his lungs by inhaling either an aerosol mist or a cloud of fine particles from an inhaler. Conventional asthma inhalers fall into two categories: 'dry powder inhalers' and 'metered dose inhalers' (MDI's).

Breath operated MDI's are known. For example U.S. Pat. No. 3565070 describes an 'inhalation actuable aerosol dispenser' and in addition WO 92/09232 and European patent 0147028 disclose further examples of breath operated MDI'S.

An MDI consists of a small canister containing medication with a metering valve and a valve stem. The MDI delivers a metered dose to the patient when the valve stem is pressed. The fundamental problem in the design of breath operated MDI's is that a large force (of the order of 30 N) is required to depress the valve stem and actuate an MDI. However only a very small force is available from the patient's breath. This problem is partly overcome in the prior art by manually compressing a large spring to a sufficient force to actuate the device. The spring is compressed by the patient, either by a positive 'cocking' process or automatically when the patient opens the mouthpiece cover. The spring is then released by a trigger operated by the patient's breath. The operation of the trigger is however difficult to engineer reliably and cheaply since releasing a spring with a stored force of 30N using a low force from the patient's breath is a difficult technical challenge.

WO 92/09323 describes a pneumatic system for holding the stored force. This requires a number of components which must be carefully manufactured to maintain a satisfactory vacuum seal during operation. European patent 0147028 describes a mechanical trigger design which requires extremely tight manufacturing tolerances and which to some extent depends on consistent levels of friction for repeatable operation.

The present invention seeks to provide an inhaler with a dose actuation mechanism which provides a very substantial amplification of the force being available from a patient's breath, whilst not being vulnerable to changes in the coefficient of friction between moving parts.

SUMMARY OF THE INVENTION

According to the present invention, there is provided a dosing device comprising a dispensing means for dispensing a dose material, and a dose actuation mechanism, in which the dose actuation mechanism comprises a readily deflectable member, and a series of at least two movable elements which transmit and magnify movement of the first element in the series to the last element in the series by a cascade effect, wherein the deflectable member is movable by airflow, and its movement is transferred to the first element of the said series so as to actuate the dispensing means.

Preferably the moveable elements are pivoted and arranged sequentially to inter-communicate, movement of a first pivoted element by the deflectable member effecting movement of at least another pivoted element so as to actuate the dispensing means.

The deflectable member is preferably movable in response to inhalation by a patient. Thus in use only inhalation by the patient is required to activate the dose actuation mechanism and thus cause the measured dose to be dispensed.

The use of a cascade of moveable pivoted elements provides a form of amplification of the originating force created by the intake of breath, and whilst any number of such elements may be employed in the cascade, in general two such elements are sufficient.

As a preferred feature of the invention, this amplification may be achieved by a first biasing means which communicates with one moveable element so that as movement is transferred between the moveable elements, energy stored in the first biasing means is released to increase the force associated with the movement. This ensures that a small initial force exerted on the deflectable member is increased in magnitude as it cascades through the moveable elements. In such a way, a small initial force is magnified to allow actuation of the dispensing means.

Preferably one moveable element remote from the deflectable member is attached to, or acts on, the dispensing means so as to restrain actuation thereof until the said moveable element is deflected as a result of a cascade action. In this way the movement of the deflectable member and the pivoted elements can be used to release stored energy to provide sufficient force to dispense a dose from the dispensing means. In particular the dispensing means may be associated with a second biasing means, in which energy is stored in compression, which stored energy is released on movement of a pivoted element.

The invention also lies in a dose actuating mechanism for use in a dosing device, comprising a deflectable member and a cascade of at least two moveable elements, movement of the deflectable member being transferred to and between the moveable elements, in such a manner as to trigger the release of stored energy sufficient to release a dose.

Preferably the dosing device is also provided with a lid including at least one cam surface, wherein movement of the lid results in the pivoted elements being restored to positions of unstable equilibrium ready to cause actuation of the dispensing means when the cascade is triggered.

The pivoted elements are preferably movable into a first position of unstable equilibrium, which movement is translated into stored energy, in the second biasing means, and when triggered, move into a second position of equilibrium, during which movement the stored energy is released from the second biasing means to dispense a dose from the dispensing means.

Preferably the moveable pivoted elements each comprise over-centre mechanisms. Thus where the over-centre mechanisms are arranged sequentially, movement of a first over-centre mechanism in the cascade, triggered by movement of the deflectable member, results in subsequent movement of the next, and in turn, any subsequent over-centre mechanisms, the last of which allows for actuation of the dispensing means.

Particularly preferred is the use of a first and a second over-centre mechanism as the moveable elements, the first over-centre mechanism communicating with first biasing means and the second over-centre mechanism communicating, via the dispensing means, with a second biasing means.

The use of two over-centre mechanisms in this way provides a force cascade which eventually results in actuation of the dispensing means. Thus an initial small force produced by movement of air due to inhalation, moves the deflectable member, which movement causes a first over-centre mechanism to shift over-centre, to produce an increased intermediate force because of the action of the first biasing means, this intermediate force in turn causes a second over-centre mechanism to shift over-centre to release a larger stored force, typically 30N, from a second biasing means, so as to operate the inhaler. The use of over-centre mechanisms allows for a very substantial force amplification whilst reducing the effect of changes in the co-efficient of friction between moving parts.

The dose actuation mechanism of the present invention is applicable to various inhalers where breath actuation is desirable and where the drug is delivered by the release of stored energy in a spring. For example there is a family of devices known as pump jets in which the drug is delivered under pressure through a nozzle by the action of a mechanical pump, typically a piston pump. These have been used in the past for nasal drug delivery and for perfumes where the droplet size is not as critical as for inhaled drugs but they are now being developed to the point where very small droplets can be produced, suitable for inhalation. The mechanical pump may be driven by a powerful spring which is released by the patient's inhalation. The present invention is suitable for this type of inhaler either used in the mouth or for nasal drug delivery.

There are also some types of dry powder inhaler (DPI) in which the release of the drug particles is assisted by air movement caused by a piston driven by the release of a compressed spring or the drug particles are mechanically released by the direct action of a triggered spring. Again there is a need for a trigger mechanism capable of being reliably triggered by a small force, and thus the present invention is also applicable for these inhalers.

The present invention is also applicable in other fields where force amplification is valuable, for example other drug delivery and medical devices where stored energy is released by a manually operated trigger. Examples of this are needle-free injection systems (both with liquid drug and powder) in which the drug is accelerated towards the patient's skin through the release of stored energy, auto-injectors in which a conventional syringe and needle are actuated by the release of stored energy and nasal or topical sprays in which the dosing pump is spring actuated.

BRIEF DESCRIPTION OF THE DRAWINGS

The invention will now be described by way of example, and with reference to the accompanying drawings in which:

FIG. 3 is a partial sectional view on the line III—III of FIG. 1 showing the first chamber of the inhaler before a dose has been supplied, line I—I is the section along which FIG. 1 is taken;

Figure 1:
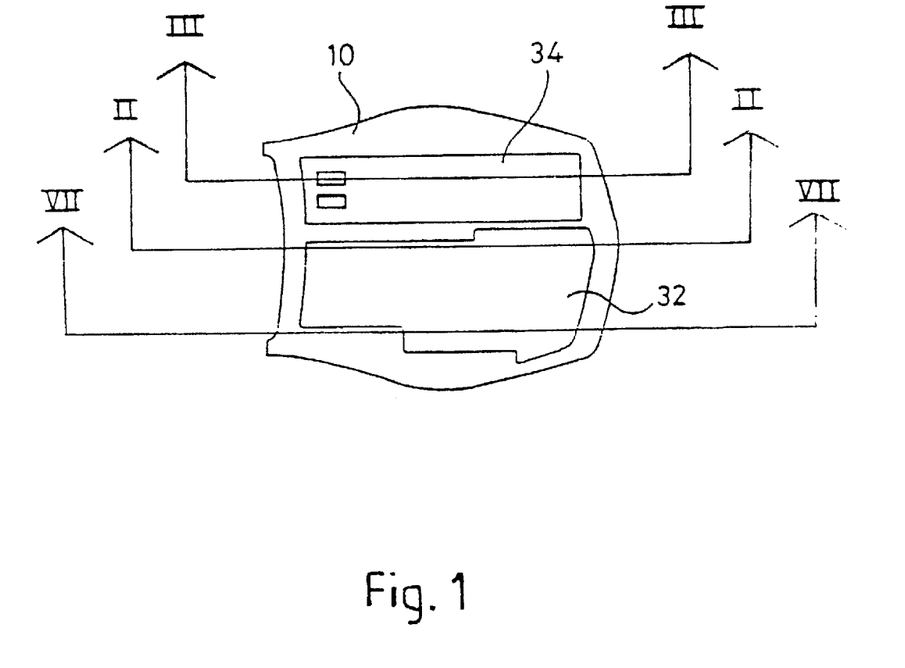
FIG. 1 is a section through a base of a breath operated meter dose inhaler according to the preset invention illustrating a first chamber and a second chamber.
Figure 2:
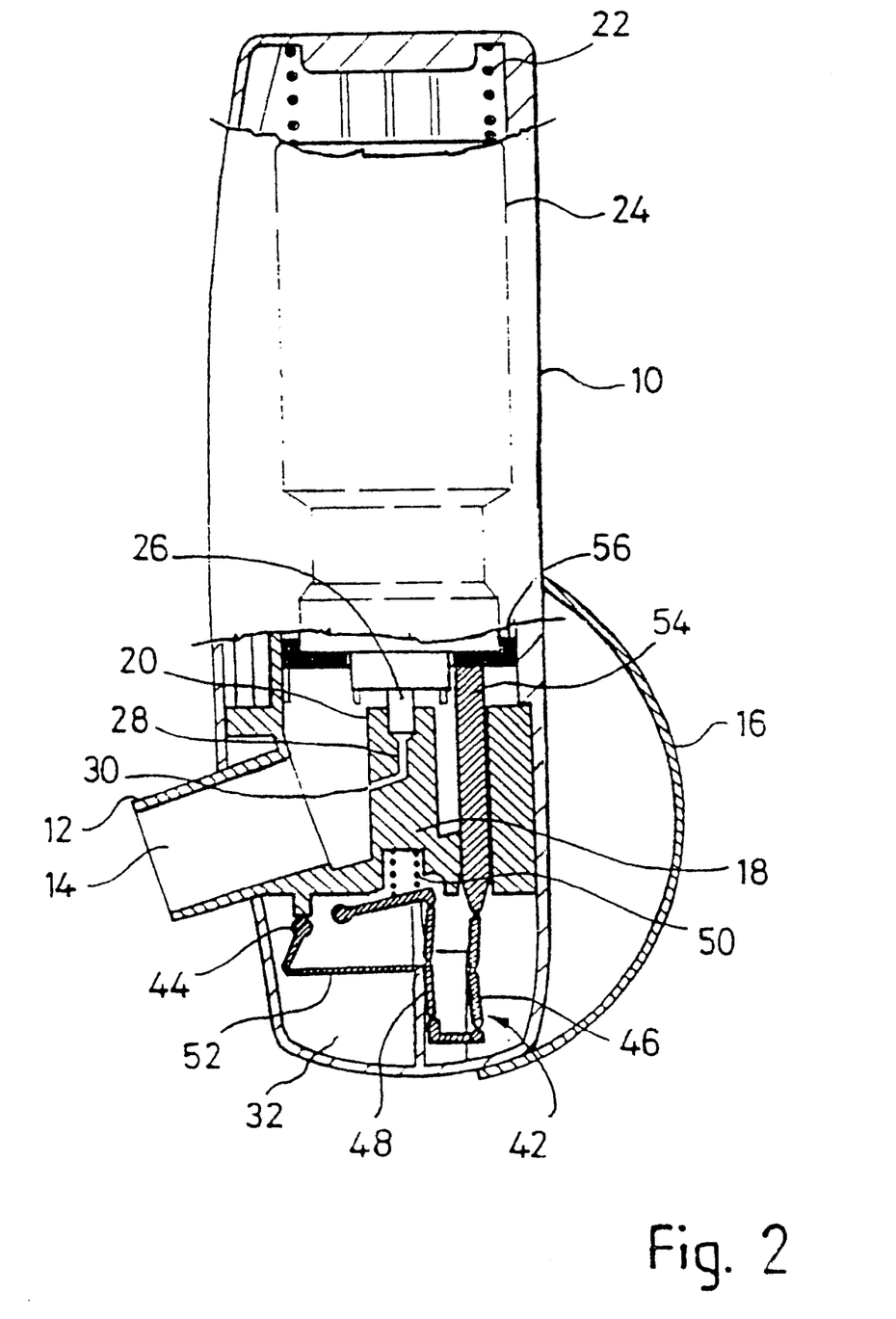
FIG. 2 is a partial sectional view on the line II—II of FIG. 1 showing the second chamber of the inhaler before a dose has been supplied.
Figure 3:
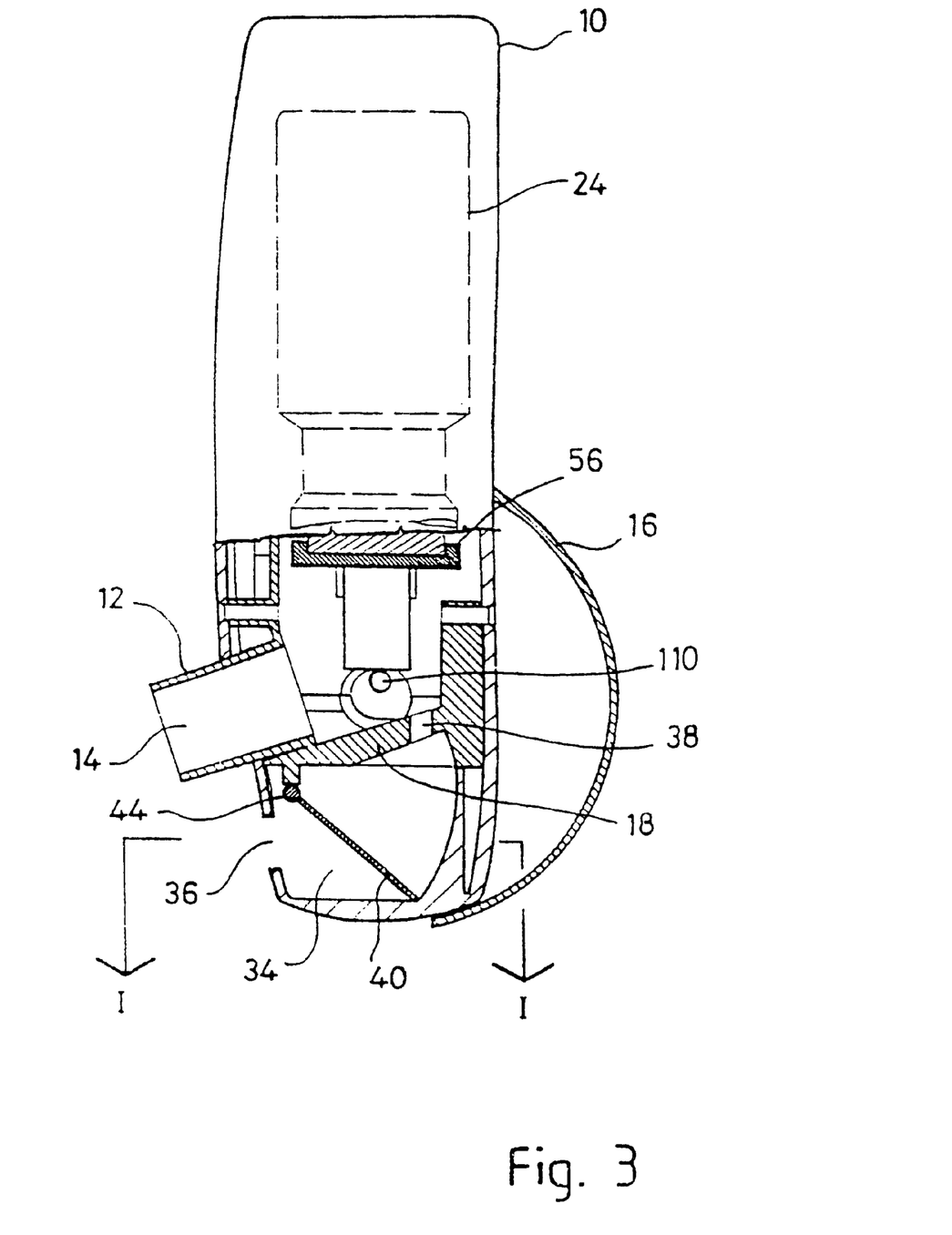

Referring to FIGS. 1, 2 and 3, a preferred embodiment of a breath operated metered dose inhaler (MDI) in accordance with the present invention comprises a hollow outer body 10, typically made of plastics material, which includes a protruding portion 12 with a central aperture 14. The protruding portion 12 and aperture 14 form a mouthpiece from which a dose may be inhaled on operation of the MDI. A mouthpiece cover 16 is pivotally attached to the outer body 10 and in FIG. 1 the mouthpiece cover 16 is shown pivoted away from the body 10 to allow access to the mouthpiece.

Internally the body 10 is provided with a supporting platform 18 bearing boss 20. A biasing means 22, such as a spring, is positioned at one end to an inner base wall of body 10 with the other end of the spring 22 engaging with a canister 24 which contains the dosing medium. The canister 24 is held between the spring 22 and the boss 20 provided on the supporting platform 18. The canister 24 is provided with a stem 26 which connects with a passage 28 within boss 20 providing a nozzle 30 through which the dose is emitted.

Two adjacent chambers 32, 34 as shown in FIG. 1 are defined within the outer body 10 by the supporting platform 18 and part of the inner wall of the lower part of outer body 10. Chamber 34 as shown in FIG. 3.provides an actuation chamber with two apertures, an inlet aperture 36 and an outlet aperture 38, so as to provide an air passage through the first chamber 34 over vane 40. An actuation mechanism 42 is contained in the second chamber 32 shown in FIG. 2 and comprises a shaft 44 which is rotatable and attached to vane 40, over-centre links 46, 48 and a biasing means 50. The shaft 44 is attached to the over-centre link 48 by a push rod 52 with over-centre link 46 being attached at one end to a neck of the canister 24 via a push rod 54 and yoke 56.

In FIGS. 2 and 3, the MDI is shown with the mouthpiece cover 16 opened and is ready for operating to provide a dose. Over-centre link 46 is held in place by the pressure of the spring 22 acting on canister 24, and thus on push rod 54. The second over-centre link 48 is held in place by the action of the small 7 spring 50. The vane 40 is shown in FIG. 3 and not in FIG. 2 because typically the vane is mounted in a separate compartment to that containing the over-centre links 46, 48, the shaft 44 and push rod 52.

Figure 4:
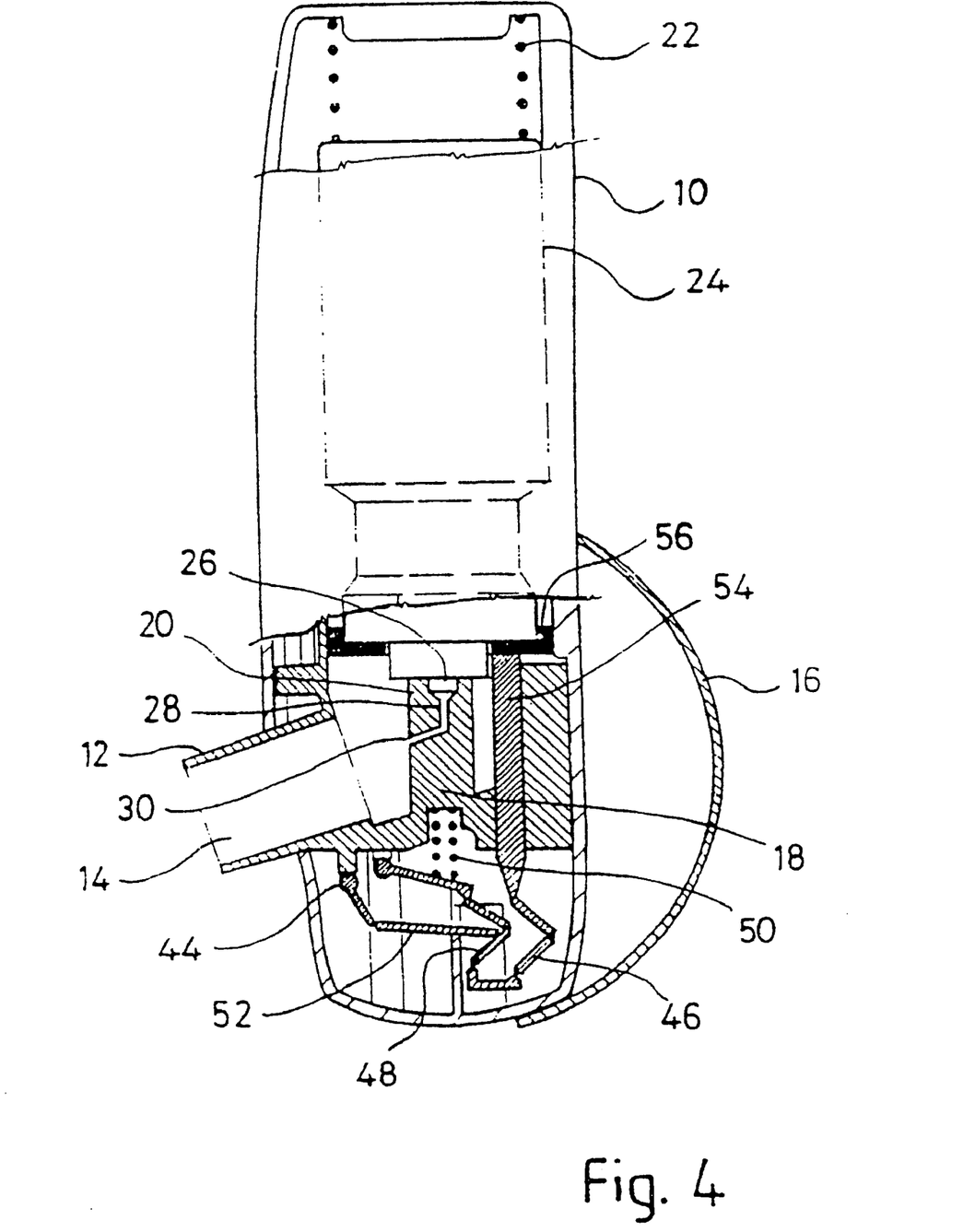
FIG. 4 is a partial sectional view on the line II—II of FIG. 1 after a dose has been supplied.
Figure 5:
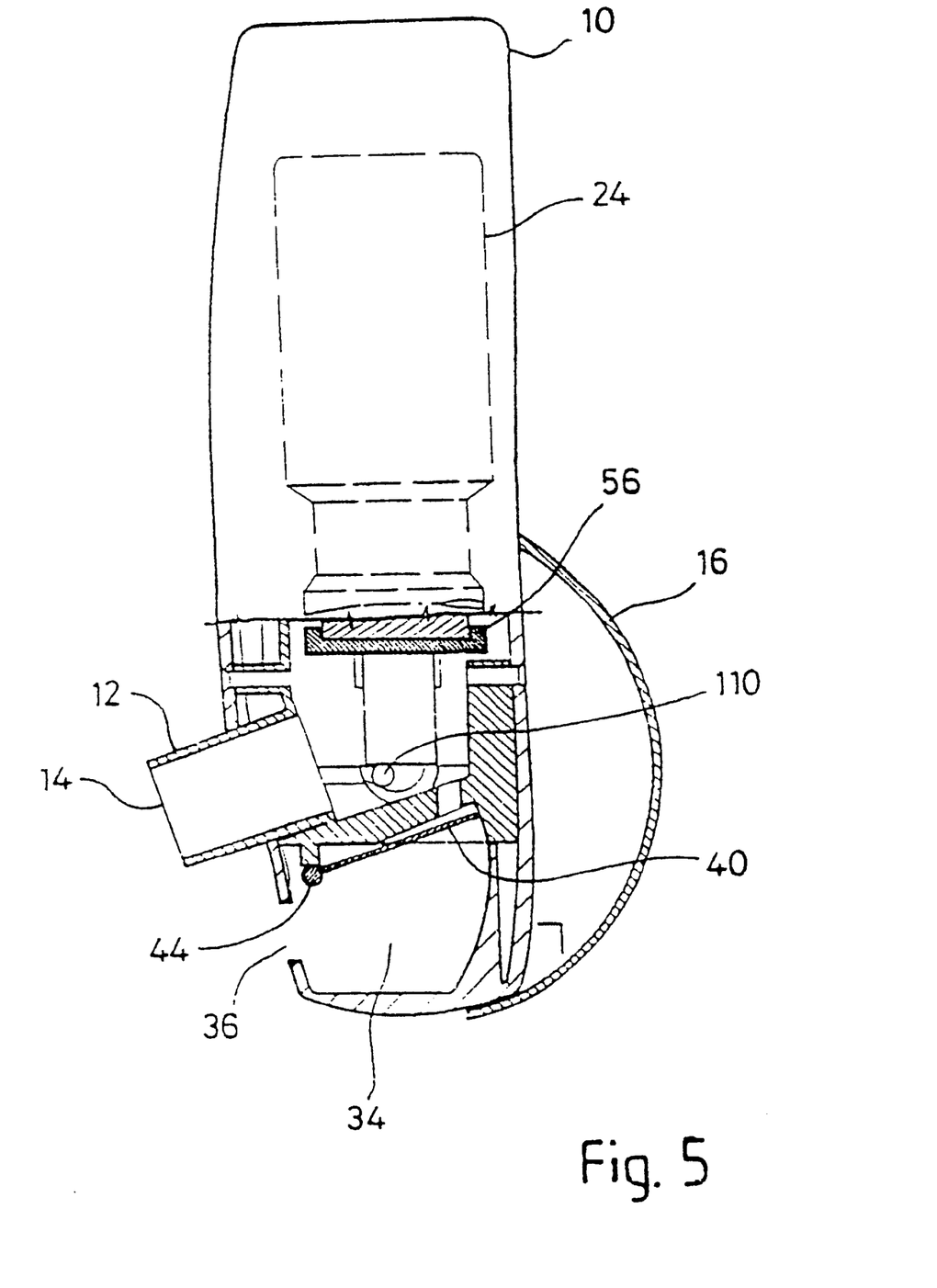
FIG. 5 is a partial sectional view on the line III—III of FIG. 1 after a dose has been supplied.

In use, a patient places his mouth over mouthpiece 12, 14 and inhales. This creates a flow of air through the chambers 32, 34, air entering from inlet aperture 36 and passing via aperture 38 into aperture 14 and thus the patient's mouth. The resulting flow of air over the vane 40 causes the vane to rotate as shown in FIG. 5 and so apply a compressive force to the push rod 52. Providing the air flow has reached a pre-determined level which is sufficient to overcome the effect of spring 50, the second over-centre link 48 moves over-centre as shown in FIG. 4. Thus the effect of the small spring 50 is to drive linkage 48 against linkage 46. The relative sizes of the springs 22 and 50 and the geometry of both the actuating chambers 32, 34 and the general internal body of the device, are selected to ensure that linkage 46 is driven over-centre by the action of linkage 48.

FIGS. 4 and 5 show the breath operated MDI after a dose has been released, with corresponding reference numerals to those used in FIGS. 1, 2 and 3 having been used for the common features. FIGS. 4 and 5 show how movement of the vane 40 results in over-centre movement of linkage 48 and subsequently linkage 46. The springs 22 and 50 are seen in their extended unbiased positions, where less energy is stored.

Figure 6A:
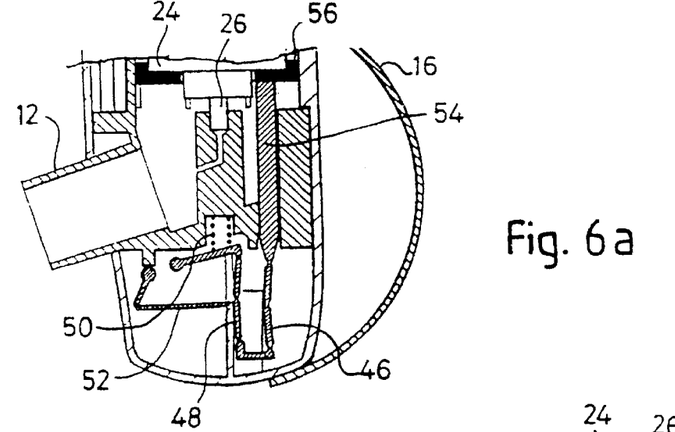
FIG. 6 is a sectional view, to an enlarged scale, on the line II—II of FIG. 1 illustrating the interaction of linkage components in the second chamber when delivering a dose.
Figure 6B:
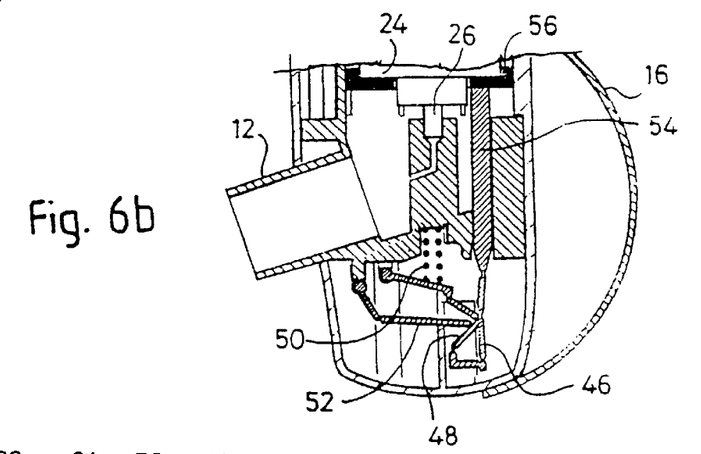
Figure 6C:
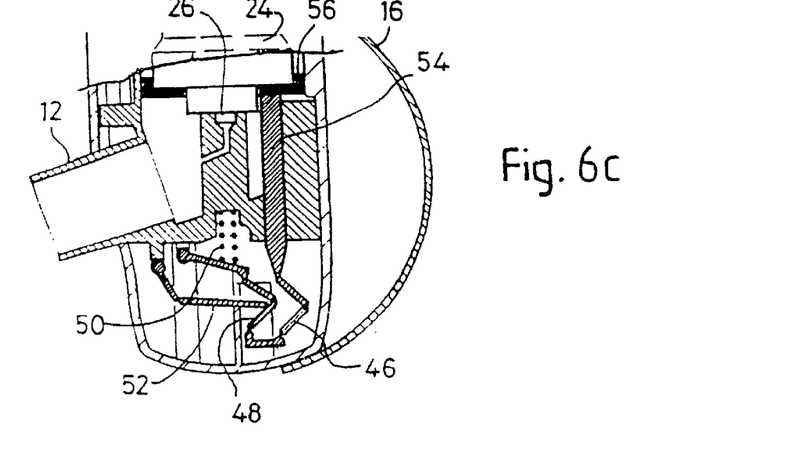

A detailed view of how the mechanism 42 works is given in FIG. 6. FIG. 6a) shows the actuation mechanism before inhalation. As inhalation occurs, a relatively small force, for example of the order of 0.25 N, in rod 52 is sufficient to displace link 48 to the right, even though a larger force, for example 3.5 N, may be stored in spring 50. In FIG. 6b), link 48 now has moved to the right and is pressing against link 46. The force of spring 50, which may have reduced to perhaps 2.5N because the spring has expanded, is sufficient to displace link 46 to the right, although link 46 is supporting a much greater force of perhaps 30N through pushrod 54. In this way the can 24 is released when the mechanism 42 collapses into the final position shown in FIG. 6c).

As linkage 46 is driven over-centre, the restraining force on the canister 24 due to the force exerted by the push rod 54 is removed and the spring 22 is free to urge the canister 24 downwards against boss 20, causing a dose to be released through stem 26.

It can be seen that over-centre link 46 exerts a force on the neck of the canister 24 so storing compressive energy in the spring 22, and similarly over-centre link 48 stores compressive energy in spring 50. On inhalation, the vane 40 is deflected by a small force from the patient inhaling, and the vane 40 moves linkage 48 releasing the stored energy in spring 50.

This results in a force cascade, the lesser force of inhalation causing an increased intermediate force at the link 48. This intermediate force is sufficient to deflect link 46, as seen in FIG. 6. As link 46 is deflected, rod 54 moves away from the neck of container 24, releasing the stored compressive energy in spring 22 and so providing a further increase in the force. Thus a force of the order of 30N is achieved, which is sufficient to dispense a dose from the stem 26.

Figure 7:
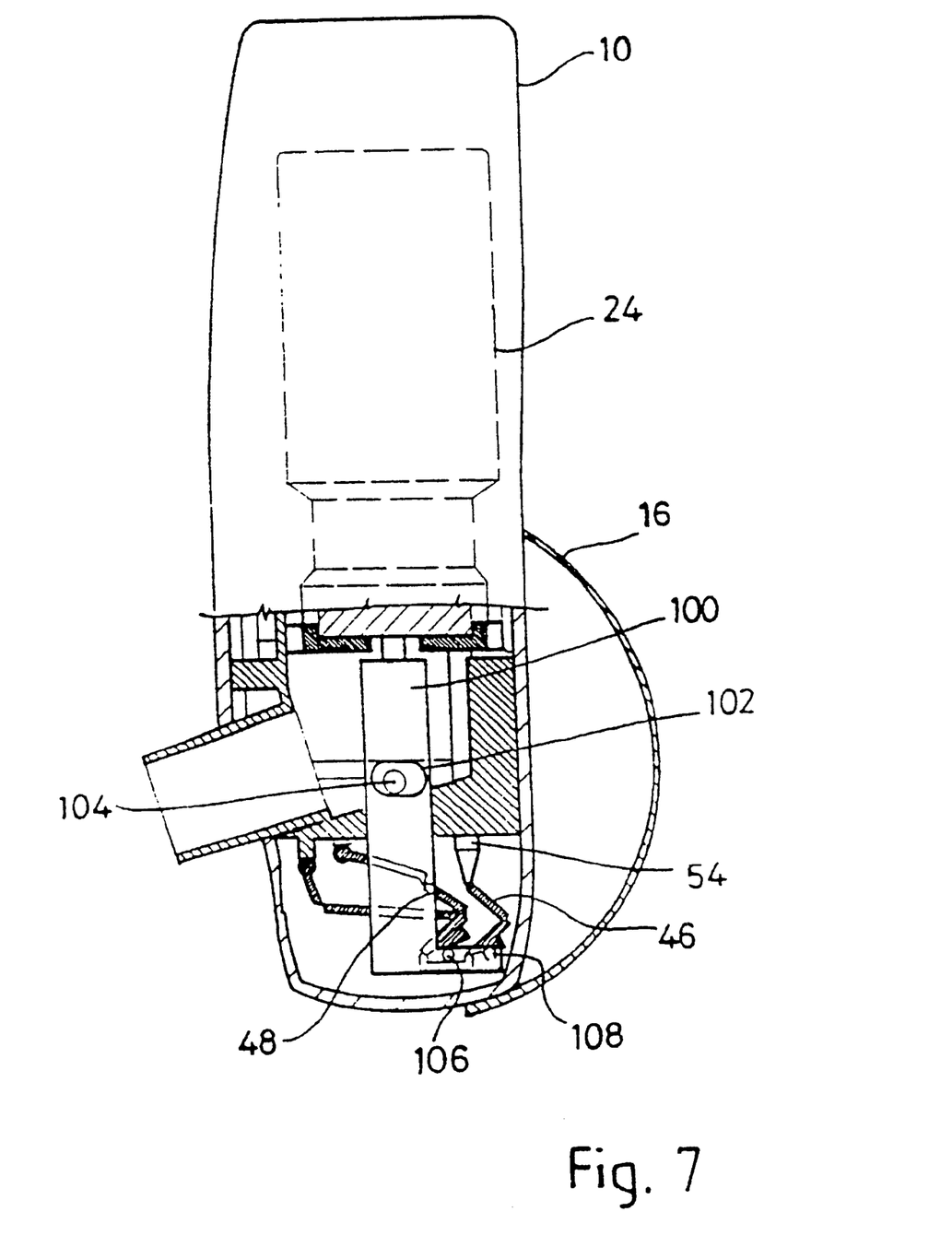
FIGS. 7 and 8 are a partial sectional view on the line VII—VII of FIG. 1 illustrating the positioning of a cam feature during operation of the inhaler.
Figure 8:
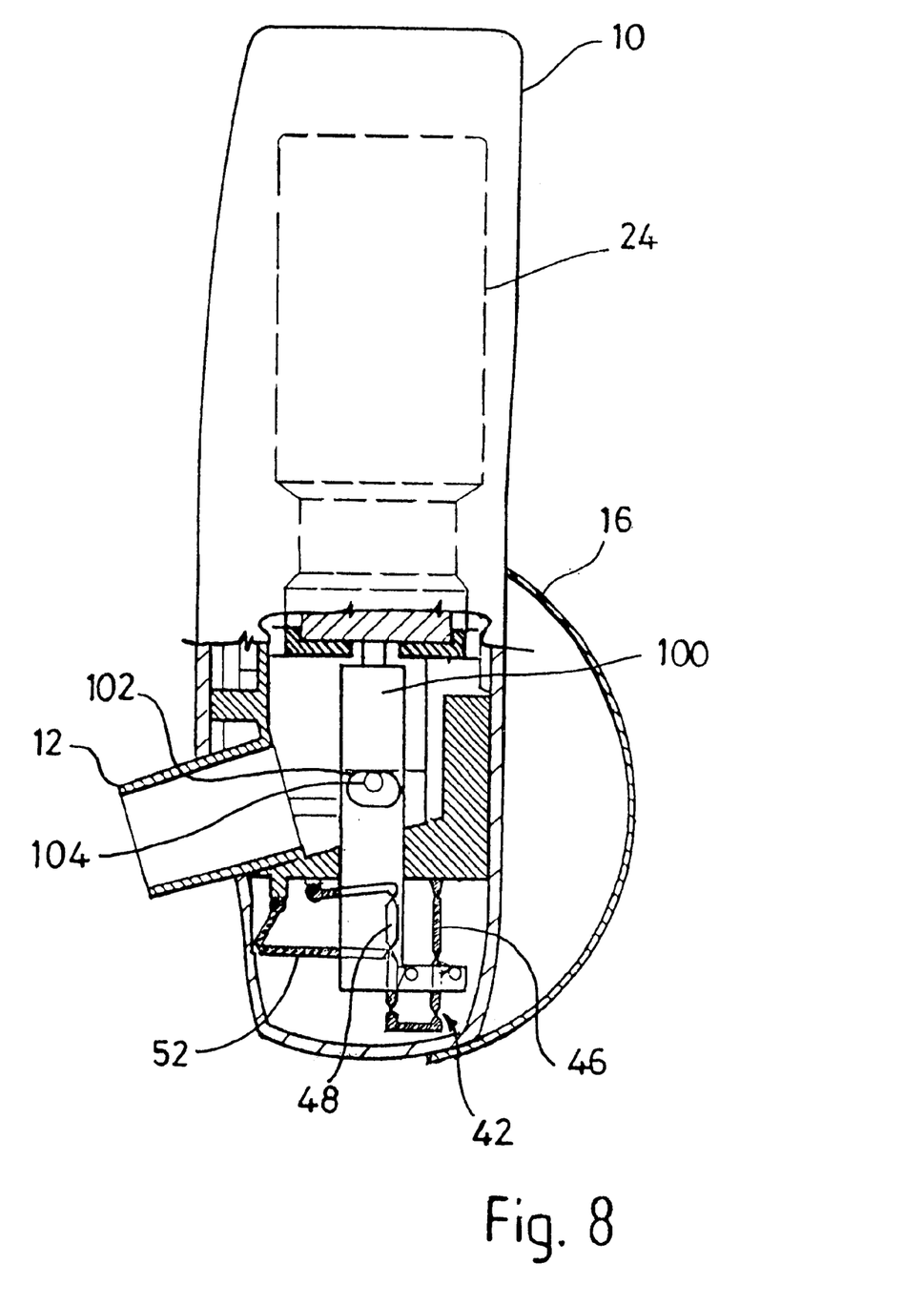

After use, the patient closes the mouthpiece cover 16 and thereby replaces the linkages to their original position. The replacement is achieved by reset link 100 as shown in FIGS. 7 and 8. At one end of the link there is a slot 102 which engages with one drive pin 104 at the pivot of the mouthpiece cover. At the other end of the reset link 100 there are two pins 106, 108 which are positioned underneath the linkages of the over-centre mechanism 46, 48. A drive pin 110 on the opposite side of the mouthpiece cover seen in FIG. 3 and FIG. 5 acts against yoke 56 to lift the canister and compress spring 22.

FIG. 7 shows the mechanism after the device has been actuated. The over-centre mechanism is dropped and the reset link 100 is in the lower position. The user then closes the mouthpiece cover.

As the mouthpiece cover closes, the two drive pins 104, 110 in the mouthpiece cover take effect. Drive pin 110 engages with yoke 56 and lifts the canister 24 upwards, compressing spring 22. Drive pin 104 is engaged in reset link 100 and lifts this link upwards. The two pins 106, 108 on the reset link then press on features in the over-centre mechanism linkage and return the linkage to an upright position. FIG. 8 shows the linkages 46, 48 and the reset link 100 in this position.

The position of the two drive pins 104, 110 in the mouthpiece cover is arranged such that the action of pin 110 is to lift the canister 24 first, before pin 104 takes effect and reset link 100 starts to move the over-centre linkage, thus avoiding an over-stressed condition for the linkages.

When the mouthpiece cover is opened, the process is largely reversed. However the size of slot 102 in the reset link 100 is larger than the diameter of pin 104, thus causing the reset link 100 to remain in position and retain the over-centre link 46 in an upright position until can 24 is lowered in place, then holding the mechanism 42 in position as shown in FIG. 8.

Figure 9:
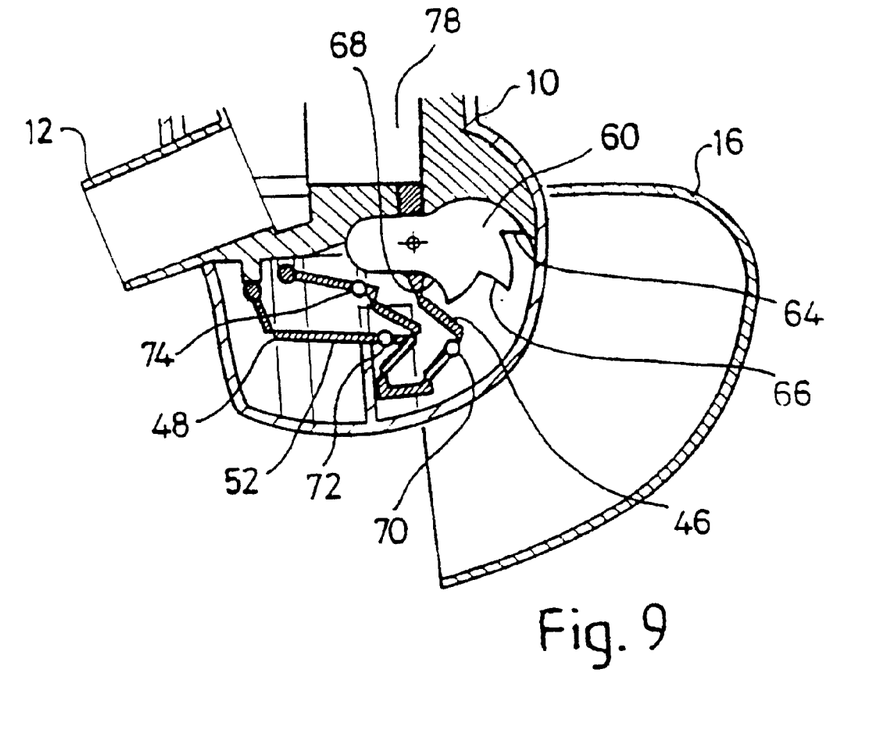
FIGS. 9 and 10 are a sectional view, to an enlarged scale, on the line VII—VII of FIG. 1 showing an alternative cam feature.
Figure 10:
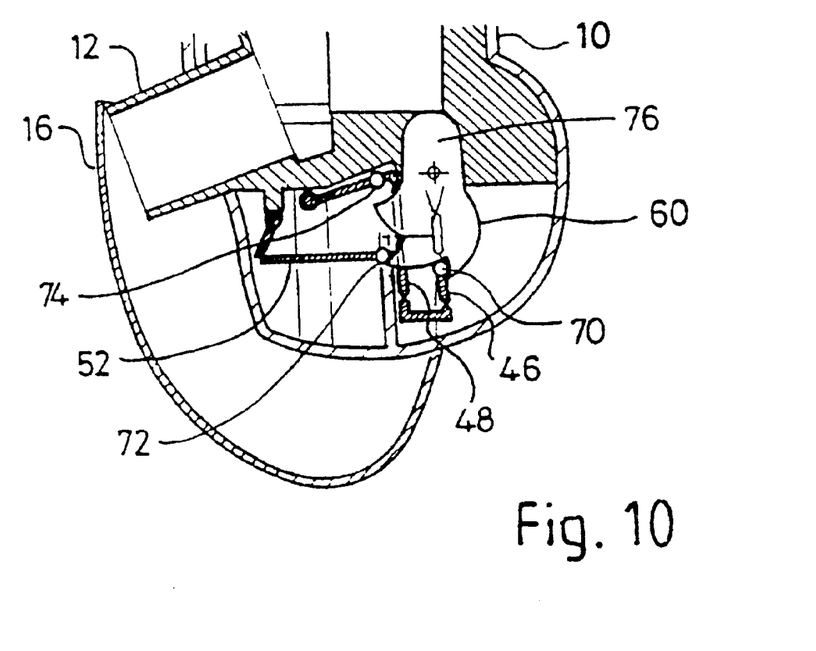

An alternative arrangement for resetting the inhaler mechanism is illustrated in FIG. 9 and 10. In this case, after use, the patient closes the mouthpiece cover 16, and cam feature 60 inside the cover 16, compress springs 22 and 50 and also returns the linkages 46 and 48 and the vane 40 to the rest, or cocked position, of FIG. 2. Cam feature 62 only acts to compress spring 22 at the same time. FIGS. 9 and 10 illustrate the cam profiles for cam 60. Cams 60 and 62 are positioned on opposite sides of cover 16, see FIG. 14. Cam feature 60 is provided on an internal wall of the mouthpiece cover 16, with cam feature 62 being provided in the corresponding position on the opposite inner wall of the cover 16, see FIG. 14. The cam features 60, 62 are designed such that during storage the smaller plastics components of the actuation mechanism 42 are not held under stress.

The cam 60 is positioned within the outer body 10, adjacent to the actuation mechanism 42. The lower part of the cam 60 has toothed portions 64, 66 and 68 which engage against pegs 70, 72 and 74 which extend to the side of the linkage mechanisms 46 and 48. In FIG. 9, the linkage mechanisms are shown dotted for clarity and this Figure shows the post-triggered condition, i.e. after delivery of a dose.

When the mouthpiece cover 16 is closed as shown in FIG. 10, the cam 60, which is directly attached to the cover 16, rotates clockwise and returns the over-centre mechanisms, or links, 46 and 48, to their starting position as required for operation of the inhaler to produce a dose. At the same time a lobe 76 provided on the cam 60 engages on a yoke 78 to lift the canister 24 and so compress the spring 22. The corresponding cam 62 provided within the mouthpiece cover 16 has a lobe identical with lobe 76, but does not have any toothed portions. By setting dimensions correctly, toothed portion 68 and lobe 76 hold the stored force from springs 50 and 22 respectively. By this means, there will be no stress on the linkages 46 and 48 during storage with the mouthpiece cover 16 closed.

The action of closing the cover 16 restores compressed energy within the biasing means so that the breath operated MDI is once again in the pre-triggering position and is capable of providing a single dose on inhalation. Thus the action of closing the cover 16 ensures the breath operated MDI is primed, priming being achieved by the interaction of the cam surfaces with the pegs and the yoke.

In the present invention, two over-centre mechanisms are used to store and release energy in the springs 22 and 50. The use of at least two over-centre mechanisms which can cascade together ensures that a very small force, as provided by a patient inhaling, can release an intermediate force stored in an intermediate spring 50 and that the intermediate force can then be used to release a larger stored force, typically 30N, which then operates the inhaler. The use of two over-centre mechanisms ensures that the inhaling force does not need to be great and that tight manufacturing tolerances are not required. The two over-centre mechanical linkages can be constructed from a very small number of parts with moulded-in flexible hinges. Thus a breath operated MDI can be provided with a trigger mechanism which does not require precise dimensions for manufacture and which is cost effective.

Figure 11A:
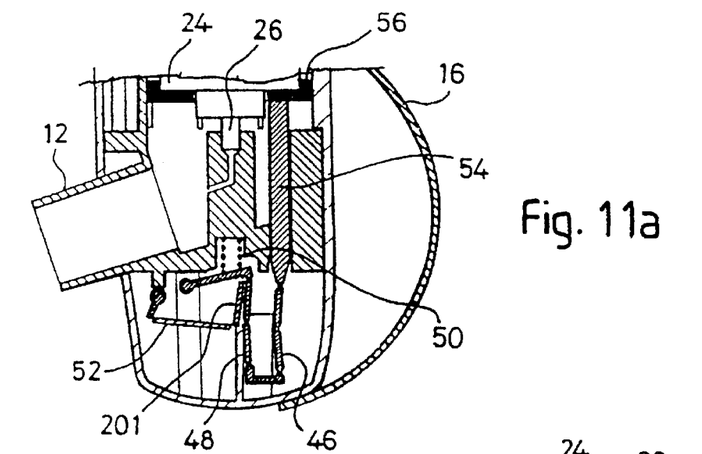
FIGS. 11 and 12 show alternative arrangements of the link mechanism and their interaction when delivering a dose.
Figure 11B:
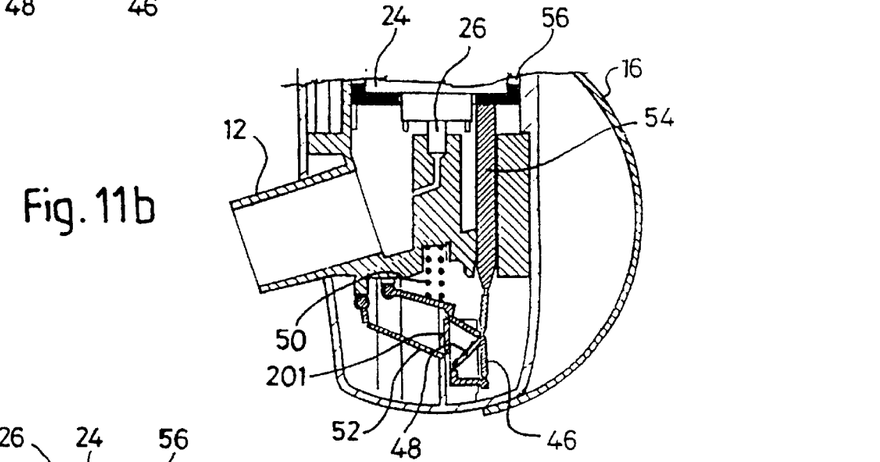
Figure 11C:
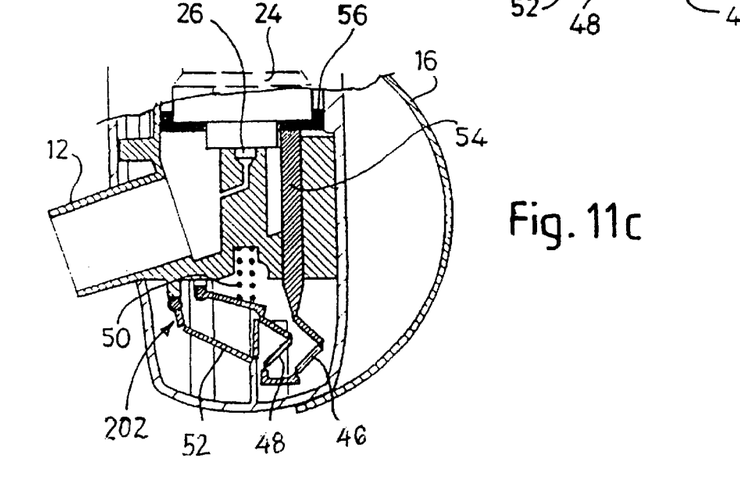

FIG. 11 shows an alternative arrangement of the link mechanism with an additional flexing piece 201 between links 52 and 48. This allows the linkage to be driven with a higher mechanical advantage as follows. FIG. 11a) shows the mechanism in the primed position. When the user inhales, the vane pivots around shaft 44 and link 52 presses to the right against link 48. When over-centre mechanism 48 collapses to the right, link 201 allows link 48 to accelerate away from link 52 as FIG. 11b). Link 48 then strikes link 46, causing the device to operate as in FIG. 11c).

The additional link 201 means that the travel required from arm 202 on shaft 44 is less than the travel required from the mechanism shown in FIG. 6. This means that arm 202 is shorter and hence the mechanical advantage available to drive the trigger mechanism is greater.

Figure 12A:
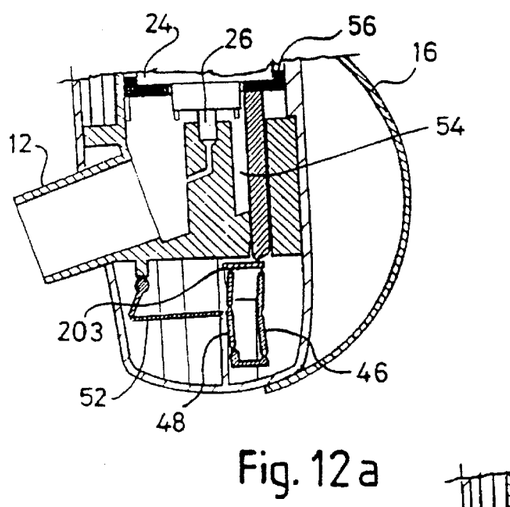
Figure 12B:
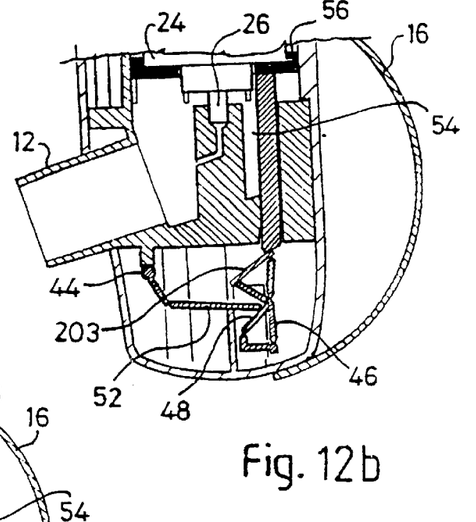
Figure 12C:
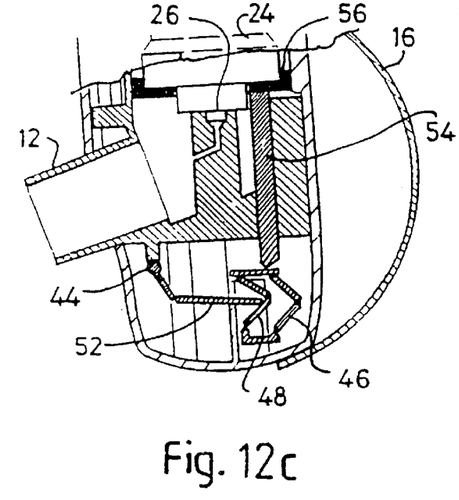

FIG. 12 shows a different alternative arrangement. In this case there is no spring 50. Instead, there is a link 203 bridging the top of mechanisms 48 and 46 and having a hinged connection to push rod 54. The effect of this is that links 48 and 46 are both held in compression by the compressive force transmitted by push rod 54 as shown in FIG. 12a) with the mechanism primed before triggering. In this position, by way of example, the compressive force in push rod 54 may be 30N. If link 203 is constructed with a 10:1 lever ratio, then the compressive forces in links 48 and 46 would be approximately 27N and 2.7N respectively. This means that link 48 can be collapsed by the use of a very low force such as 0.2 or 0.3 N in push rod 52, as described previously. FIGS. 12b) and 12c) shows the device during-operation.

The benefit of this arrangement is that spring 50 is eliminated which not only saves the cost of that component but also reduces the amount of space required by the mechanism.

Figure 13A:
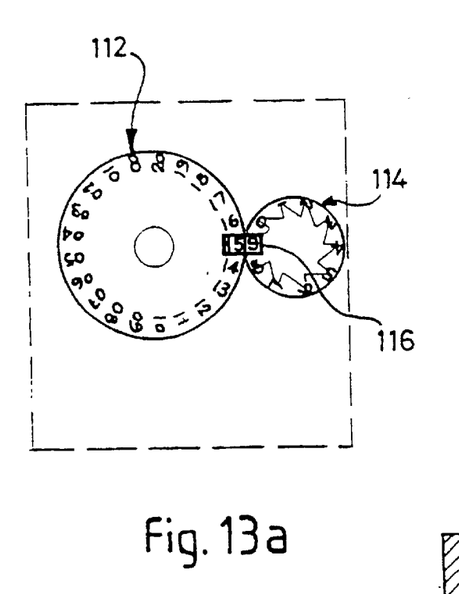
FIG. 13 shows a series of views illustrating a dose counter mechanism used with the meter dose inhaler.
Figure 13B:
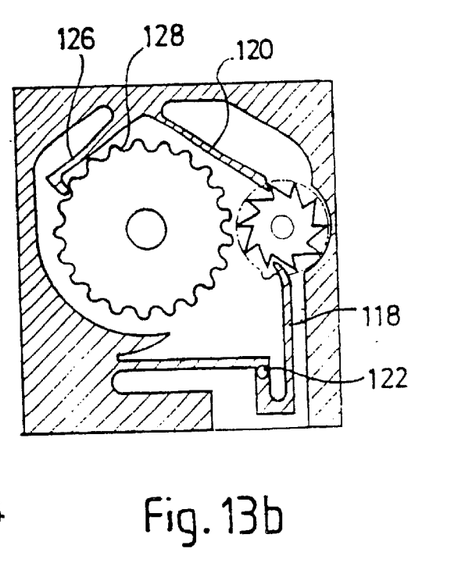
Figure 13C:
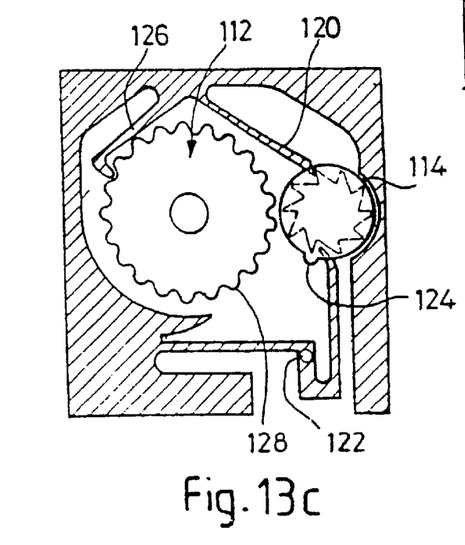
Figure 14:
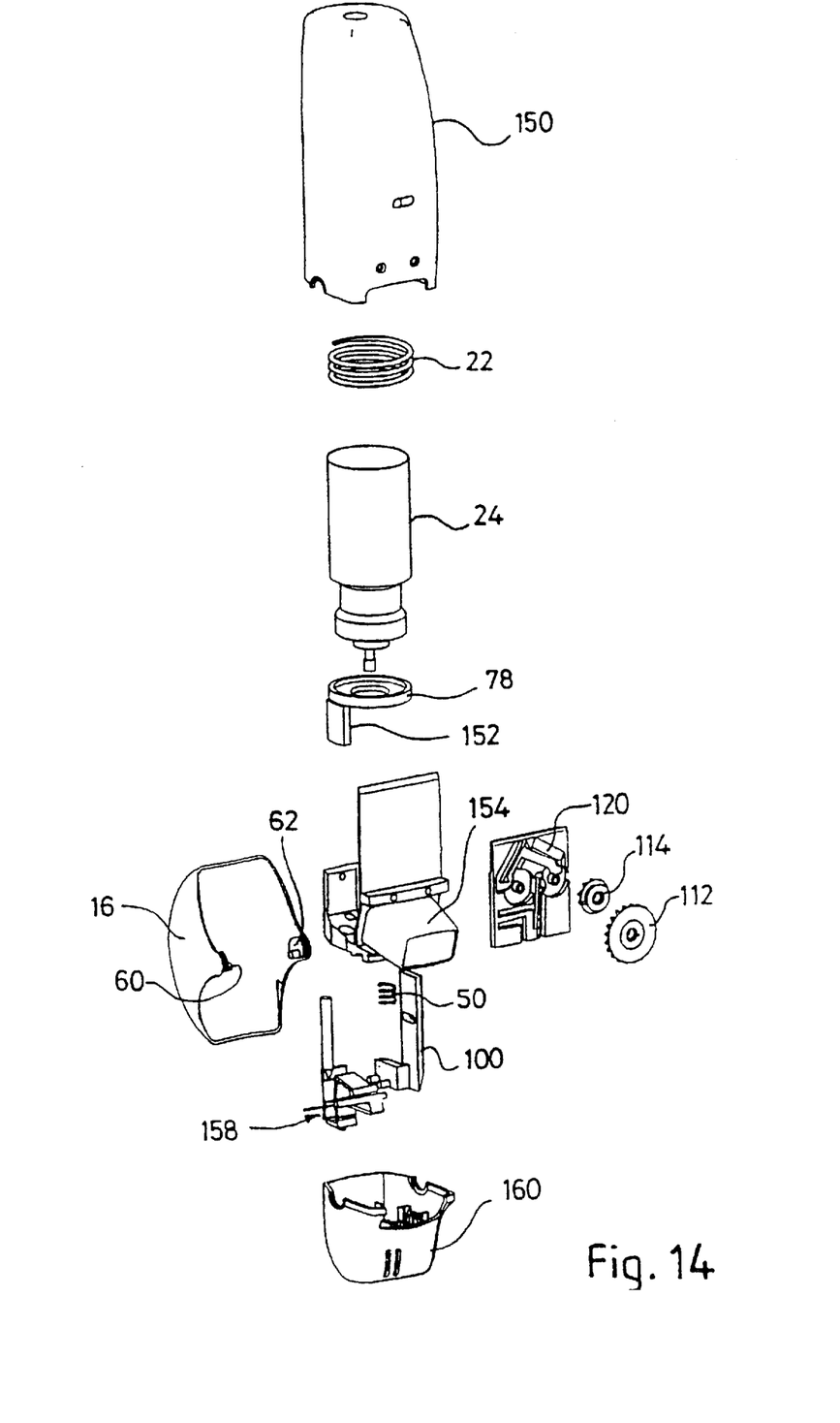
FIG. 14 is a schematic illustration showing individual components of the metered dose inhaler prior to assembly.

FIG. 13 illustrates operation of a dose counter used with the inhaler and as shown in FIG. 14. The count indication is given by two wheels 112, 114. Each wheel comprises a toothed disc portion and a smooth disc, the smooth disc of wheel 112 bearing digits 00 to 20 and wheel 114 bearing digits 0 to 9. When the wheels are viewed together through window 116, the display can show any number from 000 to 209. Typically the display is used as an indication of doses remaining for the patient, ie the display starts at, for example, 200 and counts down to 000.

Wheel 114 is driven round by the action of flexible lever 118 acting on the ratchet teeth moulded on the wheel 114. Reverse movement is prevented by the action of sprung pawl 120 acting against the same ratchet teeth.

Lever 118 contains a pin feature 122 which engages with yoke 56. When the inhaler device is actuated and reset, the can 24 moves first downwards, then upwards. This action causes lever 118 to move, which drives round wheel 114 thereby causing the counter indication to change by one unit. The design ensures that a count is only made when a dose is taken by the user. In the event of the mouthpiece cover 16 being opened and closed without a dose being taken, the can 24 will not have dropped and therefore the counter will not have been actuated.

The smooth disc of wheel 114 has a single protruding feature 124 which is designed to engage in teeth moulded into wheel 112. Once per revolution, this feature will cause wheel 112 to index its position by a single count. Thus, for example wheel 114 may change from 0 to 9, wheel 112 may change from 17 to 16 and the display would change from 170 to 169.

Sprung lever 126 is provided to engage in tooth features 128 in wheel 112 to provide a 'detent' action, retaining the wheel in its correct orientation at all times except when engaged with and driven by the wheel 114.

All the features of the counter are moulded in a single component from plastics material, thus providing a construction which is very simple and low cost.

FIG. 14 shows how a breath operated MDI in accordance with the invention could be manufactured with the actuation mechanism being composed of few separate components. FIG. 12 is an exploded view of a typical breath operated MDI, comprising an outer body 150, biasing means 22, canister 24, a yoke 78 with protruding leg 152, a mouthpiece element 154, biasing means 50, an actuating section 158, a lower cap element 160 and mouthpiece cover 16. The actuating section 158 is moulded in one piece to include both linkages 46 and 48, push rod 52, shaft 44 and vane 40. The making of multiple parts of the actuation mechanism by moulding in plastics material as a one piece actuating section 158 simplifies assembly of the breath operated MDI and reduces costs. Drive pin feature 104 is provided on an internal wall of the mouthpiece cover 16, with drive pin 110 being provided in the corresponding position on the opposite inner wall of the cover 16.

It will be apparent to a skilled person that the same effect could be achieved by counters of different physical construction including, for example, concentric indicating wheels or cylindrical indicating wheels which might provide different user benefits in terms of the size of the display digits, the size of the counter package and the number of components.

It will also be apparent to a skilled person in the art that the actuation mechanism 42 as described above may be positioned in various places within the outer body 10, for example above the canister 24, inside the biasing means 22, or alongside the canister 24. The actuation mechanism may also release the main spring 22 by the use of push rods, levers or other links as is readily apparent. The vane 40 could also be independently positioned elsewhere and linked to the two over-centre links by means other than push rod 52. The upper end of linkage 46 could be supported by a flexing arm similar to the arm linked to the upper end of linkage 48 and in such a case the connection to canister 24 could be by push rod or other mechanical link.

What is claimed is:

1. A dosing device comprising dispensing means for dispensing a dose material, a first biasing means engaging with the dispensing means, and a dose actuation mechanism comprises a deflectable member moveable by airflow, and a series of at least two moveable elements which transmit movement of the first element in the series to the last element in the series by a cascade effect, such that movement of the deflectable member is transferred to the first element of the said series and a second biasing means communicates with one of the at least two moveable elements so that as movement is transferred between the movable elements, energy stored in the second biasing means is released to increase the force associated with the movement of the moveable elements.

2. A dosing device according to claim 1, wherein the moveable elements are pivoted.

3. A dosing device according to claim 1, wherein the moveable elements are arranged to inter-communicate sequentially, so as to actuate the dispensing means.

4. A dosing device according to claim 1, wherein the deflectable member is movable in response to inhalation by a patient.

5. A dosing device according to claim 1, wherein one moveable element remote from the deflectable member is attached to, or acts on, the dispensing means so as to restrain actuation thereof until the said moveable element is deflected as a result of a cascade action.

6. A dosing device according to claim 1, further comprising a lid including at least one cam surface, wherein movement of the lid results in the moveable elements being restored to positions of unstable equilibrium ready to cause actuation of the dispensing means when the cascade is triggered.

7. A dosing device according to claim 1, wherein the moveable elements each comprise over-centre mechanisms.

8. A dosing device according to claim 1, wherein the moveable elements are a first and a second over-centre mechanism, the first over-centre mechanism communicating with first biasing means and the second over-centre mechanism communicating, via the dispensing means, with a second biasing means.

9. A dosing device according to claim 8, wherein parts of the dosing actuation mechanism are moulded as a one piece actuating section with moulded-in flexible hinges.

10. A dose activating mechanism for use in a dosing inhaler having a dispensing means for dispensing a dose material and a first biasing means fro engaging with the dispensing means, wherein the mechanism comprises a deflectable member moveable by airflow, and a cascade of at least two moveable elements, movement of the deflectable member being transferred to and between the moveable elements, wherein a second biasing means communicates with one biasing element so that as movement is transferred between the moveable elements, energy stored in the second biasing means is released to increase force associated with the movement of the moveable elements.

11. A dose actuating mechanism according to claim 10, wherein each moveable element is pivoted and comprises an over-centre mechanism.

12. A dose actuating mechanism according to claim 11, wherein the deflectable member and over-centre mechanisms are moulded as a one piece actuating section with moulded-in flexible hinges.

13. A dose actuating mechanism according to claim 10, wherein first biasing means and second biasing means communicate with the over-centre mechanisms.

\* \* \* \* \*